United States Patent
Kawaguchi et al.

(10) Patent No.: US 6,887,075 B2
(45) Date of Patent: May 3, 2005

(54) ORTHODONTIC APPLIANCE

(75) Inventors: Kozo Kawaguchi, Fukushima-ken (JP);
Kenji Nagase, Fukushima-ken (JP);
Kiyoshi Shiga, Fukushima-ken (JP);
Masaaki Orikasa, Fukushima-ken (JP)

(73) Assignee: Tomy Incorporated, Fukushima-ken (JP)

( * ) Notice: Subject to any disclaimer, the term of this patent is extended or adjusted under 35 U.S.C. 154(b) by 72 days.

(21) Appl. No.: 10/310,135

(22) Filed: Dec. 5, 2002

(65) Prior Publication Data

US 2004/0002033 A1 Jan. 1, 2004

(30) Foreign Application Priority Data

Dec. 6, 2001 (JP) ..................................... P.2001-373450
Feb. 15, 2002 (JP) ..................................... P.2002-038650

(51) Int. Cl.[7] .............................................. A61C 3/00
(52) U.S. Cl. ............................. 433/17; 433/16; 433/10; 433/11
(58) Field of Search ............................... 433/10, 11, 12, 433/13, 14, 16, 17

(56) References Cited

U.S. PATENT DOCUMENTS

| | | | |
|---|---|---|---|
| 2,195,314 A | | 3/1940 | Lincoln |
| 4,820,151 A | | 4/1989 | Pospisil |
| 5,154,606 A | * | 10/1992 | Wildman ..................... 433/8 |
| 5,314,109 A | | 5/1994 | Farzin-Nia |
| 5,358,402 A | | 10/1994 | Reed et al. |
| 5,913,680 A | * | 6/1999 | Voudouris .................... 433/10 |
| 6,257,882 B1 | | 7/2001 | Wyllie, II |

* cited by examiner

Primary Examiner—Cary E. O'Connor
Assistant Examiner—Candice C. Stokes
(74) Attorney, Agent, or Firm—Sughrue Mion, PLLC

(57) ABSTRACT

An orthodontic appliance comprises a base, a main body equipped on one side of the base, an archwire slot furnished to the main body, a convertible cap closing the archwire slot along the length direction, and stepwise portions provided at ends of the archwire slot for receiving ends of the convertible cap. The convertible cap is fixedly soldered with a silver soldering material containing Ag 90% or more.

5 Claims, 6 Drawing Sheets

ORTHODONTIC APPLIANCE

BACKGROUND OF THE INVENTION

1. Field of the Invention

The present invention relates to an orthodontic appliance to be used in a mouth.

2. Description of the Related Art

The orthodontic appliance is attached to tooth surfaces for orthodontic treatment, and serve to transmit restoring force of an archwire to a root of the teeth.

An orthodontic appliance 70 as shown in FIG. 10 comprises a base 71, a main body 72, an archwire slot 74, and a convertible cap 75. The base 71 is firmly attachable directly or indirectly to teeth. The main body 72 is equipped on one side of the base 71. The archwire slot 74 is shaped in groove along mesiodistal direction in the main body 72, and enables to support an archwire (not shown) therein. The convertible cap 75 closes the archwire slot 74 along the length direction.

In related art, a pair of ends opening in cross section of the archwire slot 74 are provided with stepwise portions 76, 76 for receiving end parts of the convertible cap 75.

The orthodontic appliance 70 is soldered by fusing and filling a silver soldering material between the ends of the convertible cap 75 and the stepwise portions 76, 76, so that the convertible cap 75 is fixed to the main body 72.

The orthodontic appliance 70 furnished with the convertible cap 75 is mainly used to first molars of upper and lower jaws, and is especially called as a convertible buccal tube.

When second molars grow, the convertible cap 75 is peeled off from the archwire slot 74, and the orthodontic appliance 70 is used similarly to an ordinary twin bracket.

In case of being used to other than, for example, the first molars and the second molars of the upper and lower jaws, the orthodontic appliance 70 is called as a convertible bracket.

As the orthodontic appliance furnished with the convertible cap, broadly known are a convertible buccal tube, convertible double tube, convertible twin buccal tube, convertible triple buccal tube, or convertible bracket.

However, the related art orthodontic appliance 70 has been involved with problems as follows.

That is, the related art orthodontic appliance member 70 is not constant in force of peeling the convertible cap 75 from the archwire slot 74. Further, there is a case the soldering is too hard to peel off the convertible cap even with an exclusively used tool (not shown). Moreover, there is a case the convertible cap 75 is carelessly removed from the archwire slot 74 with slight force.

In general, the convertible cap 75 is soldered to the stepwise portions 76, 76 of the main body 72 made of a stainless steel with a dental silver soldering material (BAg-8: Ag 72%, Cu 28%, or BAg-18: Ag 60%, Cu 30%, Sn 10%. However, in a case of fixing it only with the silver soldering material, it is seen that peeling load is largely varied depending on adhering conditions of the silver soldering material filled in a space between the convertible cap 75 and the respective stepwise portions 76, 76 of the main body 72.

The space between the convertible cap 75 and the respective stepwise portions 76, 76 of the main body 72 is mainly created by deformation of the main body 72. Since the deformation is dispersed per each of products or lots, it is extremely difficult to control the peel strength of the convertible cap effecting to the main body 72.

In addition, mainly owing to a galvanic phenomenon by different kinds of metals under conditions in the mouth, a problem has been present in corrosion occurring around soldered parts of the silver soldering material (BAg-8 or BAg-18) of the convertible cap 75.

In other words, two sorts of corrosions have existed from soldered surfaces solidified after fusion and in an interface of the soldered parts.

As to the corrosion from the soldered surface, Cu in the composition of the silver soldering material preferentially elutes, and both of the main body and the convertible cap 75 preferentially elute by influences of the eluted Cu in the interface between the main body 72 and the convertible cap 75 and the silver solder.

Therefore, the soldered strength goes down as time-passing of a teeth curing period, and when a doctor exchanges the archwire, a problem occurs that the convertible cap 75 is carelessly peeled from the archwire slot 74.

SUMMARY OF THE INVENTION

The present invention has been made in view of the above mentioned problems. Accordingly, it is an object of the present invention to provide an orthodontic appliance maintaining constant the peeling load of the convertible cap, irrespective of adhering conditions of the silver soldering material, enabling to easily peel the convertible cap from the archwire slot when needed, not weakening the peel strength of the convertible cap owing to conditions even in the mouth, and having no possibility of the convertible cap carelessly peeling off from the archwire slot.

For accomplishing the above object, the present invention is, as set forth in a first aspect thereof, an orthodontic appliance, comprising:

a base firmly attachable directly or indirectly to a tooth;

a main body equipped on one side of the base;

an archwire slot shaped in groove along mesiodistal direction in the main body, and enabling to support an archwire therein;

a convertible cap closing the archwire slot along a length direction; and stepwise portions provided at a pair of ends of an opening in cross section of the archwire slot, for receiving ends of the convertible cap, wherein the convertible cap is fixedly soldered with a silver soldering material of Ag 90% or more.

Herein, as the orthodontic appliance of the present invention, this designates general orthodontic appliances having the convertible cap. The orthodontic appliance of the present invention is applicable to, for example, the buccal tube to be used to the first molars and the second molars, and applicable to the bracket to be used to the first premolars and the second premolars of the upper and lower jaws, a cuspid, a central and lateral incisors, and a anterior tooth.

The orthodontic appliance of the present invention is applicable to a bondable type of directly fixing to the teeth with a bond, and to a weldable type of fixing to the teeth via a band crowned on the teeth.

Further, as to the soldering method by the silver soldering material, for example, one or both of the convertible cap and the stepwise portions are previously silver-plated with the silver soldering material, the end parts of the convertible cap are received in the stepwise portions, and then the main body and the convertible cap are heated by such as an electric furnace to melt the silver plate, and the silver plate with fluidity is filled in the space between the convertible cap and the stepwise portions. Otherwise, it is sufficient that a silver material previously formed in film shape of a predetermined thickness is pressed against the convertible cap to be a clad material.

Besides, as to the soldering method by the silver soldering material, the convertible cap is received at its end parts in the stepwise portions, and then the molten silver soldering material may be filled in the space between the convertible cap and the stepwise portions.

As the silver soldering material, other than Ag, e.g, optional kinds of Au, Sn, Zn or Li may be selectively contained.

In this case, if Au is contained, strength of the silver soldering material goes up, if Sn and Zn are contained, the soldering temperature of the silver soldering material may be lowered, and if Li is contained, wettability of the silver soldering material is made better.

In the thus composed orthodontic appliance, since the silver soldering material contains Ag 90% or more, the molten silver soldering material exhibits the good fluidity for soldering.

Therefore, in the orthodontic appliance, if supplying the soldering material enough to fill the space between the stepwise portions of the main body and the convertible cap, irrespective of sizes of the space, the molten silver soldering material is exactly filled in the space and can secure the convertible cap with a predetermined peel strength by bonding strength of the soldering material or strength of the soldering material itself. Therefore, it is possible to solve the related art problem that the peel strength for removing the convertible cap is not constant.

Besides, in the orthodontic appliance, since the silver soldering material contains Ag 90% or more, in other words, the Cu containing rate is lower than that of the related art silver soldering material.

Accordingly, in the orthodontic appliance of the present invention, it is possible to reduce corrosion and elution of Cu from the soldered surface, and the Cu content eluting in the soldered interface between the main body of stainless steel and the convertible cap, and maintain a desired peel strength for a longer period than that of the related art.

Further, in the present invention, as set forth in a second aspect thereof, since the silver soldering material contains Ag 99% or more, the above mentioned effect is more remarkably available.

In the present invention, as set forth in a third aspect thereof, since the silver soldering material contains no Cu, there are neither corrosion and elution of Cu from the soldered surface, nor elution of Cu content in the soldered interface between the main body of stainless steel and the convertible cap. Therefore, it is possible to maintain the peel strength for the longer period.

In addition, the present invention is, as set forth in a fourth aspect thereof, characterized in that the orthodontic appliance is the buccal tube.

Herein, as the buccal tube, there are exemplified a convertible single tube, a convertible double tube, a convertible twin buccal tube, or a convertible triple tube, and applicable teeth are not limited.

The present invention is, as set forth in a fifth aspect thereof, characterized in that each of the stepwise portions is formed in substantial dovetail in cross section.

In the thus composed orthodontic appliance, in addition to the bonding strength of the silver soldering material and a particular shearing strength, the peel strength of the convertible cap can be more controlled by plastic deformation of the dovetail groove-like stepwise portions. Further, by being fitted in the dovetail groove, the peeling load of the convertible cap can be made almost constant, irrespective of the solder adhering conditions.

DETAILED DESCRIPTION OF THE INVENTION

In the following, explanation will be made to embodiments of the orthodontic appliance of the present invention.

Figure 1:
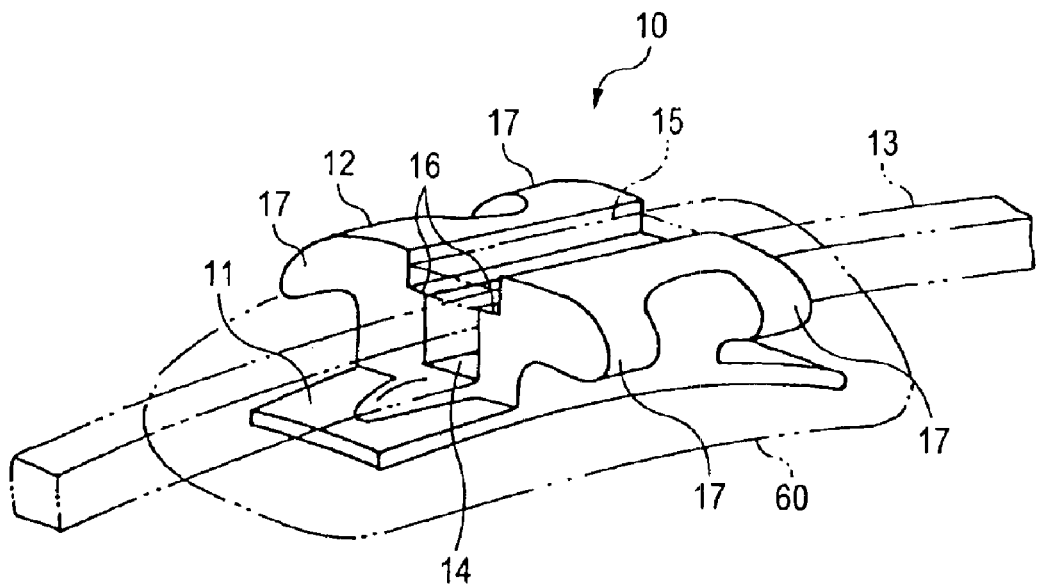
FIG. 1 is a perspective view showing the orthodontic appliance of the first embodiment according to the present invention.
Figure 2:
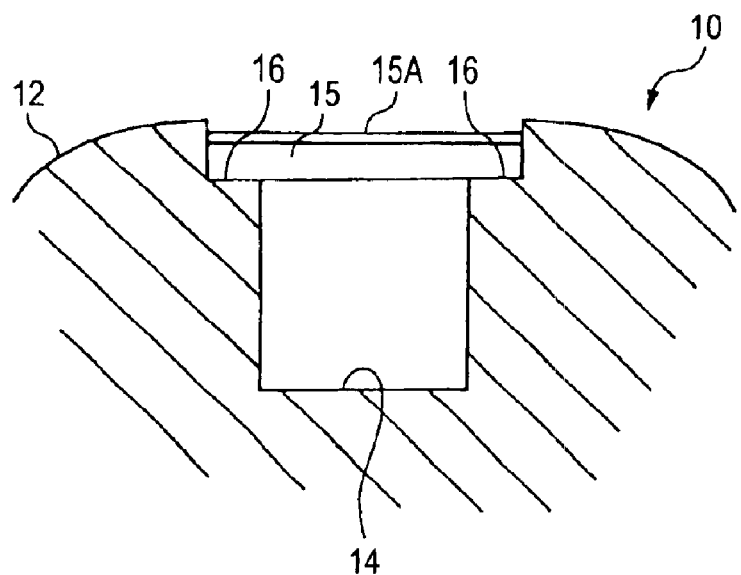
FIG. 2 is a cross sectional view enlarging the elementary parts of the orthodontic appliance of the first embodiment according to the present invention.

FIG. 1 is a view showing an orthodontic appliance of a first embodiment according to the present invention, and FIG. 2 is a cross sectional view showing the main body of the first embodiment.

As shown in FIG. 1, the orthodontic appliance 10 of the first embodiment according to the present invention comprises a base 11, a main body 12, tie wings 17, an archwire slot 14, a convertible cap 15 and stepwise portions 16, 16. The base 11 is directly attached to tooth surfaces 60 or indirectly attached thereto by welding it to a correcting band. The main body 12 is equipped on the upper surface of the base 11. The tie wings 17 expand from the main body 12 toward a gingival side and an occlusion side. The archwire slot 14 is shaped in groove along mesiodistal direction in the main body 12, and enables to support an archwire 13 therein. The convertible cap 15 closes the archwire slot 14 along a length direction. The stepwise portions 16, 16 are provided at a pair of ends in the opening in cross section of the archwire slot 14 for receiving ends of the convertible cap 15.

The orthodontic appliance 10 is used to other than, for example, the first molars and the second molars of the upper and lower jaws, and this is called as the convertible bracket.

As shown in FIG. 2, for attaching the convertible cap 15 to the respective stepwise portions 16, 16, the convertible cap 15 is performed with a silver plate 15A as an instrument for forming a silver film having a predetermined thickness on the surface of the convertible cap 15.

The Ag plate 15A contains Ag 90% or more excluding impurities, preferably 99% or more, and is a single Ag content without including Cu.

The Ag plate 15A may selectively contain, other than Ag, if needed, for example, optional kinds of Au, Sn, Zn or Li. In this case, if Au is contained, strength of the silver soldering material goes up, if Sn and Zn are contained, the soldering temperature of the silver soldering material may be lowered, and if Li is contained, wettability of the silver soldering material is made better.

The thickness of the Ag plate 15A is, for forming only the upper surface or the lower surface of the convertible cap 15, 6 to 12 $\mu$m preferably 8 to 10 $\mu$m, and for forming both surfaces, 3 to 6 $\mu$m, preferably 4 to 5 $\mu$m.

Next, the convertible cap 15 is inserted at its both end sides into the stepwise portions 16, 16. At this time, an instrument such as a spot welder may be used to temporarily hold them. Then, this assembly is heated for 30 to 60 minutes in a hydrogen atmospheric electric furnace keeping 1000 to 1100° C.

The Ag plate 15A of the convertible cap 15 is fused thereby and enters between both end sides of the convertible cap 15 and the stepwise portions 16, 16, so that the convertible cap 15 is soldered to the stepwise portions 16, 16.

The peeling load of the convertible cap 15 soldered through the above sequence was measured by an exclusively used tester. The test results show large improvements of the peel strength of the convertible cap 15 in comparison with the related art ones. The results are shown in Table 1.

By the way, the exclusively used tester has been made by an assignee company of this invention, in which a wedge of a distal angle being 30 degree is entered into the archwire slot 14 from the mesial side, and the convertible cap 15 is peeled off from the main body 12, and pushing loads at this time were measured.

TABLE 1

Comparison of peeling load between BAg-8, 3 $\mu$m and Ag, 8 $\mu$m

Comparative Example 1: BAg-8, 3 $\mu$m one-side plate

22 Slot single

|  | 69-162-05 | 69-362-80 | 69-462-09 | 69-162-15 | 69-262-05 |
|---|---|---|---|---|---|
| MEAN | 12.16 | 11.04 | 12.43 | 9.87 | 10.74 |
| S.D. | 2.67 | 2.17 | 1.74 | 2.93 | 2.23 |
| MAX | 17.02 | 15.07 | 16.97 | 16.80 | 16.76 |
| MIN | 7.42 | 7.78 | 8.44 | 5.00 | 7.13 |
| N | 50 | 10 | 50 | 50 | 50 |

Example 1: Single silver composition, Silver 8 $\mu$m one-side plate

22 Slot single

| N = 45 | 69-162-05 | 69-362-80 | 69-462-09 | 69-162-15 | 69-262-05 |
|---|---|---|---|---|---|
| MEAN | 9.55 | 9.83 | 10.73 | 10.74 | 9.08 |
| S.D. | 1.08 | 1.47 | 1.44 | 1.56 | 1.12 |
| MAX | 12.08 | 12.80 | 13.59 | 14.94 | 11.16 |
| MIN | 7.71 | 6.15 | 7.08 | 6.99 | 6.94 |

In Table 1, Example 1 is the orthodontic appliance 10 of the above mentioned first embodiment. Comparative Example 1 is the related art orthodontic appliance Ag-plated of 3 $\mu$m of BAg-8 (Ag 72% and Cu 28%) on one side heated at 950° C or 30 minutes in the hydrogen atmosphere in the same items of the same lot.

A hypercomplex silver solder as the related art BAg-B or BAg-18 is high in the bonding strength and in the mechanical strength of the silver soldering material itself. Therefore, if supplying the silver soldering material of such an amount completely filling the space between the main body and the convertible cap, probably the soldering is too hard to peel off the convertible cap even with the exclusively used tool.

The peel strength at this time was 20 kg or more according to the measured results by the above mentioned tester.

Accordingly, Comparative Example 1 was designed to be plated of 3 $\mu$m thickness on one side not to completely fill the space between the main body and convertible cap, but owing to the production lots, the spaces were filled or not filled, and as seen in Table 1, the constant peel strength of the convertible cap could not be obtained.

This can be understood by magnification of standard deviations (S.D.) of Comparative Example 1 in Table 1.

On the other hand, Example 1 was designed to be plated of 8 $\mu$m thickness of the single silver composition to completely fill the space between the main body and convertible cap, so that comparatively constant peeling load could be obtained. The standard deviations (S.D.) of 1.0 or lower are not rare depending on the lots.

Since, in the peeling strength, Example 1 is around ½ of Comparative Example 1 (20 kg or more when completely filled), very approximate values to optimum values being 7 to 12 kg by the above mentioned tester can be obtained.

Besides, since, in Comparative Example 1, the elution temperature of BAg-8 is 780° C. and the elution temperature of BAg-18 is 600 to 720° C., the soldering temperature is near to a heat treatment temperature in a sensitization range causing stress corrosion cracking of stainless steels.

However, in Example 1, the silver soldering material has a single silver composition, a melting point of Ag is 960° C., and the soldering temperature is within a range of 1000 to 1100° C. Therefore, the soldering temperature of Example 1 exists in ranges of solidifying the stainless steels and of a bright heat treatment, so that the austenite stainless steel such as the convertible cap is merely softened and easily deformed, thus conveniently peeling off the convertible cap.

The stainless steel of a precipitation hardening group can accomplish objective strength and hardness through the following heating treatment.

Thus produced Comparative Example 1 and Example 1 were immersed in an artificial saliva for 62 days, and images of the peeled soldered boundaries by immersion are shown in FIGS. 3A, 3B and 4A, 4B.

Figure 3A:
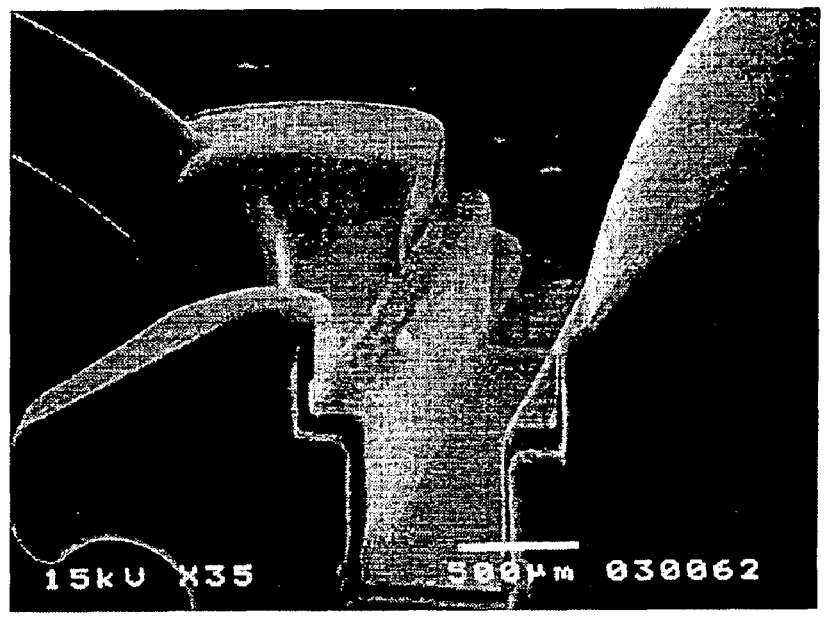
FIGS. 3A and 3B are images enlarging the elementary part of Comparative Example 1.
Figure 3B:
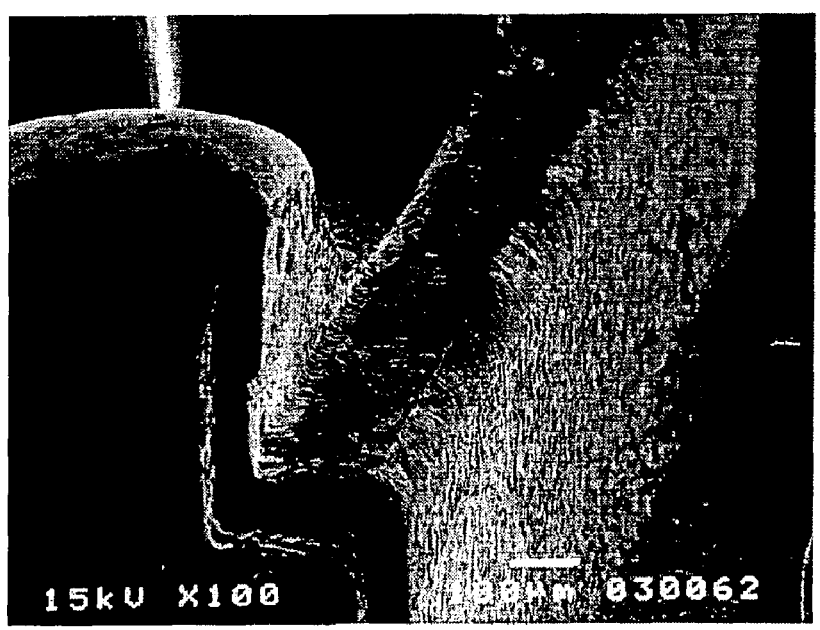

FIGS. 3A and 3B are images enlarging the elementary parts of Comparative Example 1, wherein FIG. 3A is the image magnifying the elementary part by 35 times, and 3B is the image magnifying the elementary part by 100 times.

Figure 4A:
FIGS. 4A and 4B are images enlarging the elementary part of Example 1.
Figure 4B:
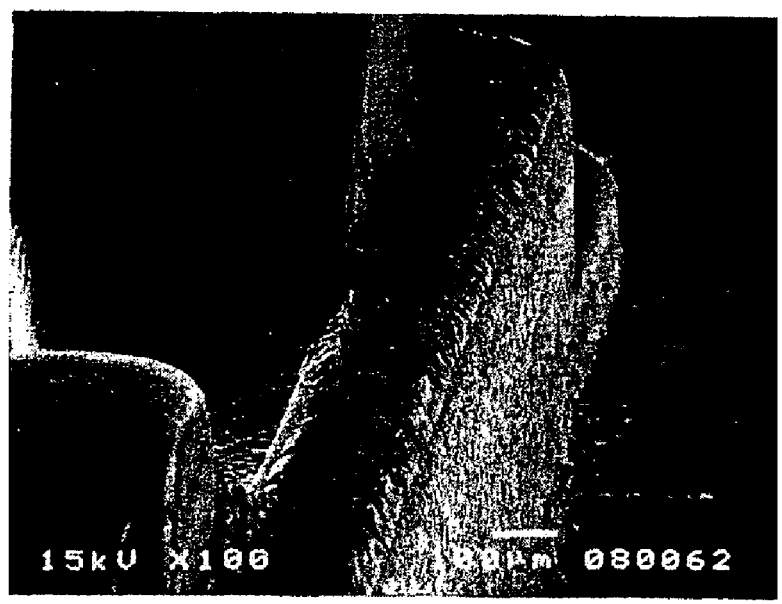

On the other hand, FIGS. 4A and 4B are images enlarging the elementary parts of Example 1, wherein FIG. 4A is the image magnifying the elementary part by 35 times, and 4B is the image magnifying the elementary part by 100 times.

The data of the peeling load of Comparative Example 1 and Example 1 are shown in Table 2, and the elution test data are shown in Table 3.

TABLE 2

Changes of peeling load by artificial saliva as time-passing at immersion for two months (Unit: kgf)

| | Comparative Example 1 hypercomplex silver solder BAg-8, 3 μm one-side plate | | | | | | Example 1 Single silver composition Silver 8 μm one-side plate | | | | |
|---|---|---|---|---|---|---|---|---|---|---|---|
| | MEAN | S.D. | MIN | MAX | Down rate (%) | | MEAN | S.D. | MIN | MAX | Down rate (%) |
| Before immersion | 10.76 | 1.64 | 8.62 | 13.52 | — | Before immersion | 9.19 | 1.41 | 6.62 | 12.37 | — |
| Before one day | 9.03 | 1.42 | 7.00 | 11.62 | 16.1 | Before one day | 8.43 | 1.18 | 6.94 | 10.38 | 8.2 |
| Before 2 days | 9.35 | 1.79 | 7.53 | 12.16 | 13.1 | Before 2 days | 8.96 | 1.23 | 6.81 | 10.81 | 2.5 |
| Before 5 days | 7.61 | 2.75 | 4.46 | 12.11 | 13.1 | Before 5 days | 8.57 | 0.67 | 7.76 | 9.88 | 6.8 |
| Before 7 days | 6.07 | 1.74 | 4.32 | 10.49 | 43.6 | Before 7 days | 8.80 | 1.10 | 7.14 | 10.31 | 4.2 |
| Before 9 days | 7.28 | 1.73 | 4.85 | 9.78 | 32.4 | Before 9 days | 9.35 | 0.96 | 7.26 | 10.64 | |
| Before 16 days | 5.71 | 1.58 | 4.35 | 9.47 | 46.9 | Before 16 days | 8.58 | 1.13 | 6.31 | 10.12 | 6.6 |
| Before 19 days | 5.75 | 1.12 | 4.04 | 7.45 | 46.5 | Before 19 days | 8.40 | 1.23 | 6.54 | 9.99 | 8.6 |
| Before 23 days | 7.56 | 2.62 | 4.13 | 11.31 | 29.8 | Before 23 days | 8.79 | 1.13 | 7.25 | 10.47 | 4.4 |
| Before 26 days | 5.50 | 1.74 | 2.64 | 8.18 | 48.8 | Before 26 days | 8.97 | 1.51 | 6.68 | 11.51 | 2.4 |
| Before 31 days | 7.28 | 2.13 | 4.80 | 11.66 | 32.4 | Before 31 days | 8.96 | 1.05 | 7.42 | 10.63 | 2.5 |
| Before 62 days | 5.38 | 1.51 | 3.34 | 8.84 | 50.0 | Before 62 days | 8.65 | 1.12 | 6.41 | 9.85 | 5.9 |

TABLE 3

Elusion amount by artificial saliva (Unit: ppb)

| | Comparative Example 1 hypercomplex silver solder BAg-8, 3 μm one-side plate | | | | | | Example 1 Single silver composition Silver 8 μm one-side plate | | | | |
|---|---|---|---|---|---|---|---|---|---|---|---|
| | Ag | Fe | Ni | Cu | Cr | | Ag | Fe | Ni | Cu | Cr |
| Before one day | 1.8 | 2.5 | 0.6 | 16.5 | 0.3 | Before one day | 8.8 | 3.2 | 1.2 | 33.3 | 0.3 |
| Before 2 days | 7.6 | 3.0 | 1.2 | 37.0 | 0.5 | Before 2 days | 8.8 | 1.8 | 1.8 | 50.8 | 0.7 |
| Before 5 days | 2.3 | 4.4 | 1.9 | 86.2 | 1.2 | Before 5 days | 3.9 | 3.0 | 2.3 | 67.6 | 1.3 |
| Before 7 days | 2.3 | 11.2 | 5.8 | 60.3 | 1.9 | Before 7 days | 9.5 | 4.7 | 3.0 | 74.7 | 0.8 |
| Before 9 days | 3.3 | 16.4 | 9.1 | 53.7 | 2.9 | Before 9 days | 15.3 | 4.3 | 3.2 | 61.2 | 1.1 |
| Before 16 days | 3.9 | 88.2 | 18.6 | 92.9 | 15.8 | Before 16 days | 41.1 | 38.2 | 5.8 | 61.8 | 7.1 |
| Before 19 days | 12.3 | 126.6 | 22.0 | 99.2 | 25.5 | Before 19 days | 46.1 | 30.9 | 6.4 | 69.8 | 6.0 |
| Before 23 days | 6.8 | 71.3 | 15.1 | 95.0 | 11.9 | Before 23 days | 30.4 | 34.8 | 6.3 | 61.3 | 6.8 |
| Before 26 days | 15.8 | 105.4 | 17.8 | 81.5 | 16.5 | Before 26 days | 40.7 | 35.8 | 6.5 | 46.2 | 6.5 |
| Before 31 days | 4.9 | 74.4 | 16.7 | 66.6 | 11.3 | Before 31 days | 32.1 | 38.3 | 7.2 | 51.2 | 7.1 |
| Before 62 days | 24.9 | 424.6 | 42.6 | 96.3 | 86.3 | Before 62 days | 57.6 | 57.8 | 10.3 | 51.2 | 12.2 |

As seen in FIGS. 3A and 3B, in the soldered interface of comparative Example 1, the elution of the silver soldering material is recognized, and besides, in particular, the stepwise portions of the main body made of the stainless steel are largely corroded and eluted.

Comparing with this, as seen in FIGS. 4A and 4B, not only the elution of the silver soldering material is not recognized from the soldered interface of Example 1, but also the degree of corrosion of the main body is small.

This is comprehended from the peeling load as time-passing in Table 2. That is, a hypercomplex silver solder on one side of 3 μm of BAg-8 in Comparative Example 1 was around 10 kg prior to immersion in an artificial saliva, but after two months passed, it was reduced to half.

In contrast, the solder of single silver composition in Example 1 is scarcely changed.

Further, according to the elution test data of Table 3, it is seen that the Cu content elute in comparatively high density from initial periods in both of the hypercomplex silver solder of BAg-8 in Comparative Example 1 and the solder of single silver composition in Example 1.

In the hypercomplex silver solder of BAg-8 in Comparative Example 1, the Cu content of the soldered surface at first elute, and as the density of the eluted Cu becomes higher, the main body of stainless steel in the vicinity of the soldered interface is extremely corroded. This is comprehended from rapid increase thereafter of Fe, Ni and Cr in the contents of the stainless steel.

On the other hand, in the solder of single silver composition in Example 1, the elution of the Cu content of the stainless steel of the precipitation hardening group (Cu: 3.0 to 5.0%) is recognized, but the degree of the stainless steel itself is small.

Figure 5:
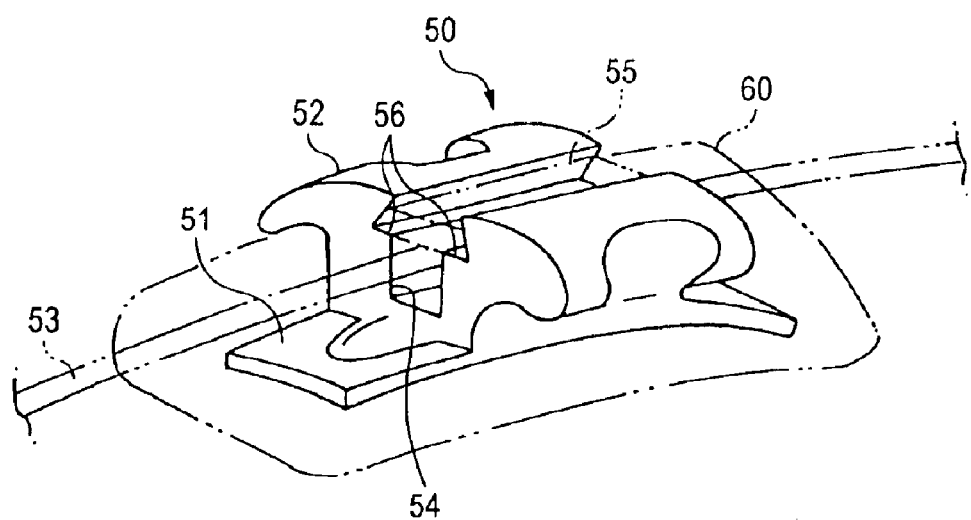
FIG. 5 is a perspective view showing the orthodontic appliance of the second embodiment according to the present invention.
Figure 6:
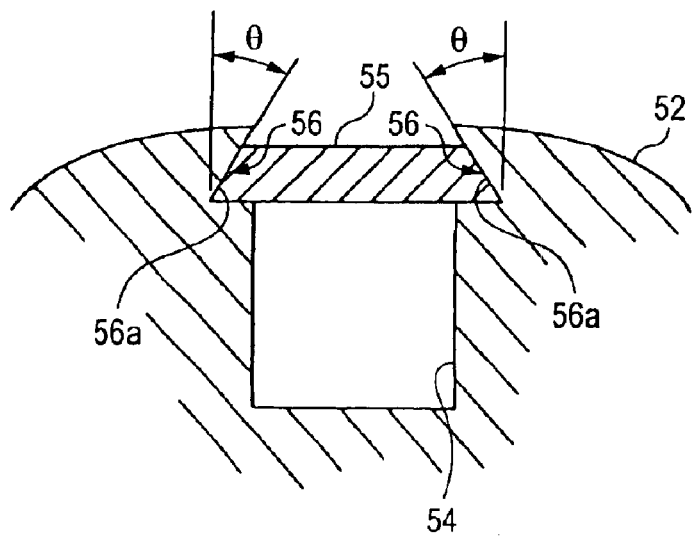
FIG. 6 is a cross sectional view enlarging the elementary parts of the orthodontic appliance of the second embodiment according to the present invention.

FIGS. 5 and 6 show an orthodontic appliance 50 according to second embodiment according to the present invention.

The orthodontic appliance 50 of the second embodiment has stepwise portions 56, 56 formed substantially in dovetail groove in cross section. A convertible cap 55 is almost trapezoidal in cross section of, e.g., the austenite stainless steel.

The convertible cap is inserted into the stepwise portions 56, 56 from the mesial side and soldered.

In the second embodiment, an angle 0 of inclination of the stepwise portions 56, 56 is around 10 to 15 degree with respect to a vertical line.

Similarly to the above mentioned first embodiment, the convertible cap 55 silver-plated 8 μm on one side is inserted into the stepwise portions 56, 56 from the mesiodistal direction, and soldered under the same conditions to the first embodiment.

If the soldered convertible cap 55 is peeled from the mesial side by use of the exclusive tool, the end parts of the convertible cap 55 and the inclined faces 56a, 56a of the stepwise portions 56, 56 scrape each other, and both are destroyed. Therefore, the stepwise portions 56, 56 and the convertible cap are effected with shear fracture over the full length in the mesiodistal direction.

Thereby, the peeling load is made more constant, not influenced by the adhering conditions of the soldering material.

Figure 7:
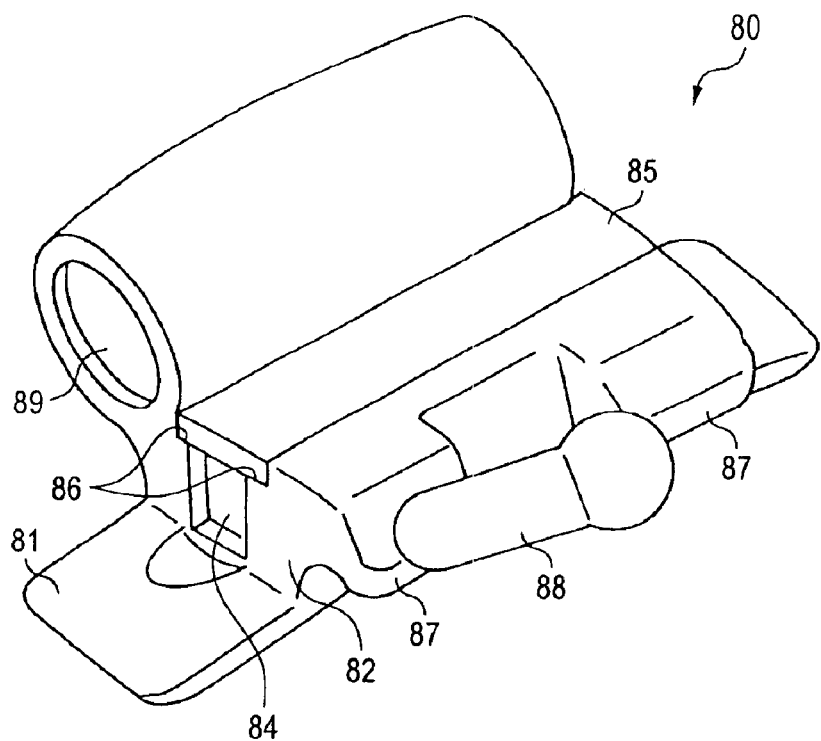
FIG. 7 is a perspective view showing the orthodontic appliance of the third embodiment according to the present invention.

FIG. 7 shows an orthodontic appliance 80 according to a third embodiment of the present invention.

The orthodontic appliance 80 of the third embodiment comprises a base 81, a main body 82, tie wings 87, a hook 88, a tube 89, an archwire slot 84, a convertible cap 85 and stepwise portions 86, 86. The main body 82 is equipped on the upper surface of the base 81. The tie wings 87 expand from the main body 82 toward a gingival side. The hook 88 is connected to the tie wings 87. The tube 89 is installed in opposition to the tie wings 87 and inserted with a face bow and an end of a lip bumper. The archwire slot 84 is shaped in groove along the mesiodistal direction in the main body 82, and enables to support an archwire therein. The convertible cap 85 closes the archwire slot 84 along the length direction. The stepwise portions 86, 86 are provided at an opening in cross section of the archwire slot 84.

The orthodontic appliance 80 is called as a convertible double tube to be used to the first molars and the second molars of the upper and lower jaws.

The present invention is applicable to such the orthodontic appliance 80.

Figure 8:
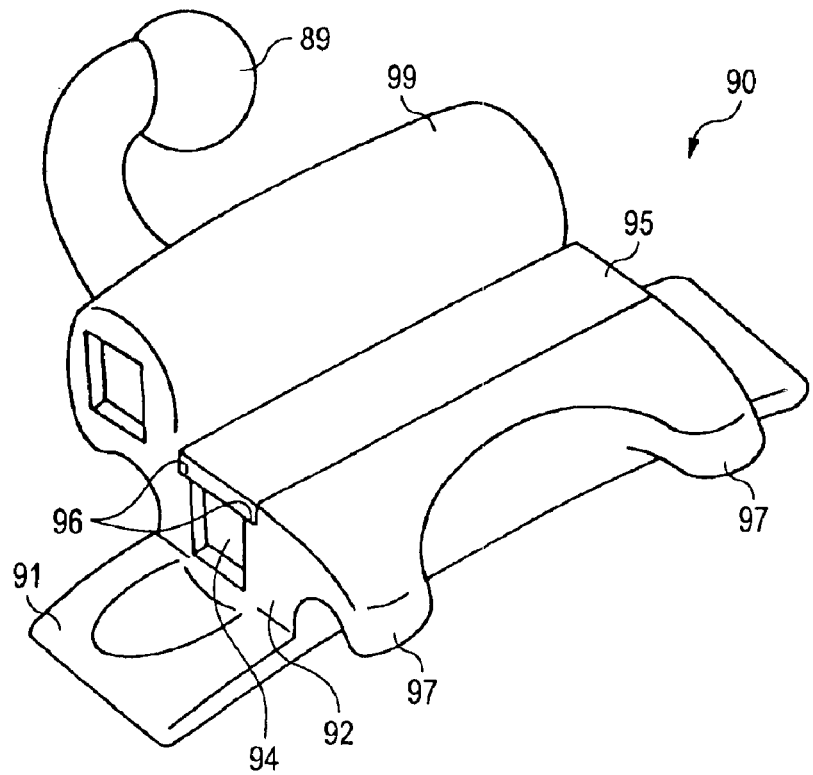
FIG. 8 is a perspective view showing the orthodontic appliance of the fourth embodiment according to the present invention.

FIG. 8 shows an orthodontic appliance 90 according to a fourth embodiment of the present invention.

The orthodontic appliance 90 of the fourth embodiment comprises a base 91, a main body 92, tie wings 97, a tube 99 for an auxiliary wire, a hook 98, an archwire slot 94, convertible cap 95 and stepwise portions 96, 96. The main body 92 is equipped on the upper surface of the base 91. The tie wings 97 expand from the main body 92 toward the occlusal side. The tube 99 for an auxiliary wire is installed in opposition to the tie wings 97 and inserted with the auxiliary wire. The hook 98 is connected to the tube 99. The archwire slot 94 is shaped in groove along mesiodistal direction in the main body 92, and enables to support a main archwire therein. The convertible cap 95 closes the archwire slot 94 along a length direction. The stepwise portions 96, 96 are provided at an opening in cross section of the archwire slot 94.

The orthodontic appliance 90 is called as a convertible twin buccal tube to be used to the first molars and the second molars of the upper and lower jaws.

The present invention is applicable to such the orthodontic appliance 90.

Figure 9:
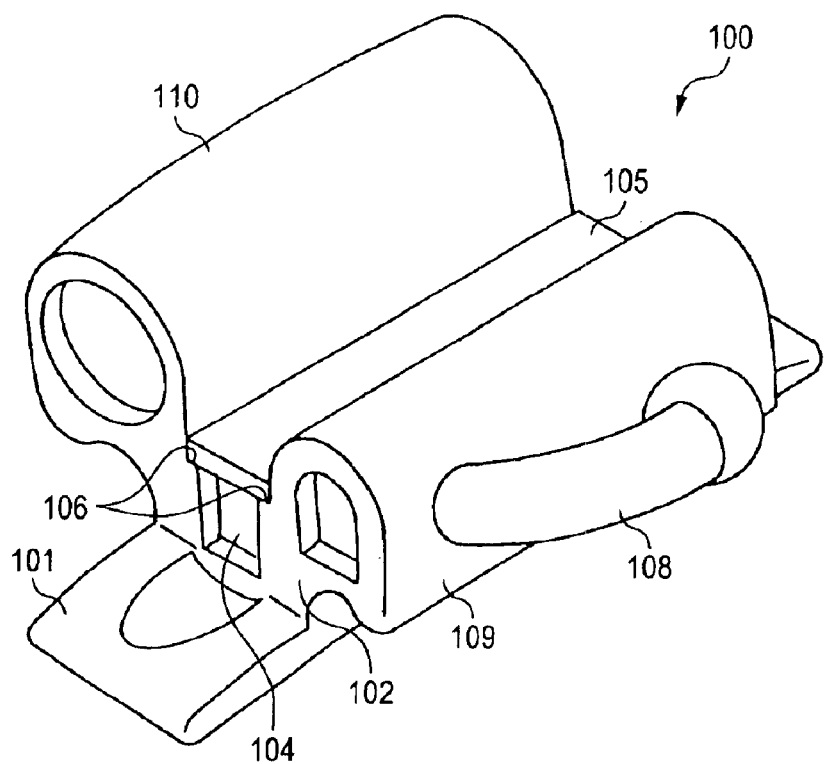
FIG. 9 is a perspective view showing the orthodontic appliance of the second embodiment according to the present invention.
Figure 10:
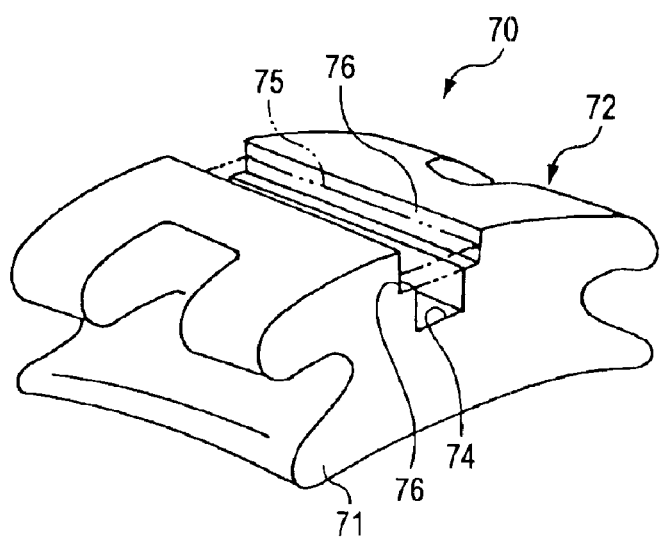
FIG. 10 is a perspective view showing the related art orthodontic appliance.

FIG. 9 shows an orthodontic appliance 100 according to a fifth embodiment of the present invention.

The orthodontic appliance 100 of the fifth embodiment comprises abase 101, a main body 102, a tube 109 for an auxiliary wire, a tube 110, a hook 108, an archwire slot 104, a convertible cap 105, and stepwise portions 106, 106. The a main body 102 is equipped on the upper surface of the base 101. The tube 109 for an auxiliary wire is installed in the gingival side of the main body 102 and inserted with the auxiliary wire. The tube 110 is installed at an occlusion side of the main body 102 and inserted with the face bow and the ends of the lip bumper. The hook 108 is connected to the tube 109 for the auxiliary wire. The archwire slot 104 is shaped in groove along mesiodistal direction in the main body 102, and enables to support a main archwire therein. The convertible cap 105 closes the archwire slot 104 along the length direction. The stepwise portions 106, 106 are provided at an opening in cross section of the archwire slot 104.

The orthodontic appliance 100 is called as a convertible triple buccal tube to be used to the first molars of the upper and lower jaws.

The present invention is also applicable to such the orthodontic appliance 100.

By the way, in the above mentioned embodiments, the Ag plate is exemplified as the instrument of forming Ag-film of predetermined thickness on the surface of the convertible cap, and the Ag-film forming instrument also includes a clad material where the silver material formed in film having in advance a predetermined thickness is pressurized to the convertible cap.

As explained above, according to the present invention, as set forth in the first aspect thereof, since the silver soldering material contains Ag 90% or more, it exhibits the well conditioned fluidity. Further, by supplying the soldering material enough to fill the space between the stepwise portions of the main body and the convertible cap, irrespective of the sizes of the space, the molten silver soldering material is exactly filled in the space. Moreover, owing to the bonding strength of the soldering material or the strength of the soldering material itself, the convertible cap man be fixed at the predetermined peel strength.

In addition, in this orthodontic appliance, since the silver soldering material contains Ag 90% or more, in other words, the Cu content is lower than that of the related art silver soldering material, it is possible to reduce corrosion and elution of Cu from the soldered surface, and the Cu content eluting in the soldered interface between the main body of stainless steel and the convertible cap, and maintain the desired peel strength for a longer period than that of the related art.

Further, according to the present invention, as set forth in the second aspect thereof, since the silver soldering material contains Ag 99% or more, the above mentioned effects are more available.

Still further, according to the present invention, as set forth in the third aspect thereof, since the silver soldering material contains no Cu, there are neither corrosion and elution of Cu from the soldered surface, nor elution of Cu content in the soldered interface between the main body of stainless steel and the convertible cap. Therefore, it is possible to maintain the peel strength for the longer period.

According to the present invention, as set forth in the fourth aspect thereof, being the buccal tube, the present invention is broadly useful to the orthodontic appliance of the convertible cap type.

Yet further, according to the present invention, as set forth in the fifth aspect thereof, since the stepwise portions are formed in substantial dovetail groove in cross section, in addition to the bonding strength of the silver soldering material and a particular shearing strength, the peel strength of the convertible cap can be more controlled by plastic deformation of the dovetail groove-like stepwise portions. Further, the convertible cap is fitted in the dovetail groove, the peeling load of the convertible cap can be made almost constant, irrespective of the solder adhering conditions.

What is claimed is:

1. An orthodontic appliance comprising:
   a base firmly attachable directly or indirectly to a tooth;
   a main body equipped on one side of the base;
   an archwire slot shaped in groove along mesiodistal direction in the main body, enabling to support an archwire therein;
   a convertible cap closing the archwire slot along a length direction;
   stepwise portions provided at a pair of ends of an opening in cross section of the archwire slot for receiving ends of the convertible cap,
   wherein the convertible cap is fixedly soldered with a silver soldering material containing Ag 90% or more.

2. The orthodontic appliance as set forth in claim 1, wherein the silver soldering material contains Ag 99% or more.

3. The orthodontic appliance as set forth in claim 1, wherein the silver soldering material contains no Cu.

4. The orthodontic appliance as set forth in claim 1, wherein the orthodontic appliance is a buccal tube.

5. The orthodontic appliance as set forth in claim 1, wherein each of the stepwise portions is formed in substantial dovetail in cross section.

* * * * *